United States Patent [19]

Berns et al.

[11] Patent Number: 5,028,426
[45] Date of Patent: Jul. 2, 1991

[54] DELETION MUTANT OF PSEUDORABIES VIRUS AND VACCINE CONTAINING SAID VIRUS

[75] Inventors: Antonius J. M. Berns, Spaarndam; Arnold L. J. Gielkens, Lelystad; Robertus J. M. Moormann, Swifterbant, all of Netherlands

[73] Assignee: Centraal Diegeneeskundig Instituut, Leystad, Netherlands

[21] Appl. No.: 78,751

[22] Filed: Jul. 28, 1987

Related U.S. Application Data

[63] Continuation-in-part of Ser. No. 44,043, May 1, 1987, abandoned, which is a continuation of Ser. No. 660,097, Oct. 12, 1984, Pat. No. 4,680,176.

[30] Foreign Application Priority Data

Oct. 12, 1983 [NL] Netherlands .................. 8303501

[51] Int. Cl.$^5$ ................ A61K 39/12; C12N 15/00; C12N 7/04
[52] U.S. Cl. ................. 424/89; 435/172.3; 435/236; 435/172.1; 435/235.1
[58] Field of Search ........... 435/235, 236, 172.1, 435/172.3; 424/89

[56] References Cited

U.S. PATENT DOCUMENTS 4,322,404  3/1982  Gauri et al.
4,514,497  4/1985  Kit et al. ........................ 435/235
4,609,548  9/1986  Kit et al. ........................ 424/89
4,680,176  7/1987  Berns et al. .................... 424/89

FOREIGN PATENT DOCUMENTS 0074808  3/1983  European Pat. Off.
0141458  5/1985  European Pat. Off.

OTHER PUBLICATIONS

Joklik et al. (eds.) 1980 in: 17th Edition *Zinsser Microbiology*, Appleton-Century-Crofts/New York, pp. 1119-1121.
Brock, T. D., 1979, in: *Biology of Microorganisms* 3rd Ed. Prentice-Hall, Inc. pp. 504-505.
Tenser et al (1983) J. Gen. Virol. 64, 1369-1373.
Tenser et al. (1983) J. Clin. Microbiol. 17, 122-127.
Ben-Porat et al. (1983) Virol. 127, 194-204.
Gielkens et al. (1982) in: *Current Topics in Vet. Med. and Animal Sci.* pp. 3-13.
de Leeuw et al. (1982) Vet. Qtrly. 4, 49-56.
Paul, P. S., et al.: "Differentiation of Pseudorabies (Aujeszky's Disease) Virus Strains by Restriction Endonuclease Analysis", *Archives of Virology*, 73, (1982), pp. 193-198.
Ihara, Seiji, et al.: "Comparison of the Physical and Genetic Maps of Pseudorabies Virus Shows that the Genetic Map is Circular", *Virology*, 122, (1982), pp. 268-278.
Rixon, Frazer J., Jr., et al.: "Structural Evolution of the DNA of Pseudorabies-Defective Viral Particles", *Virology*, 97, (1979), pp. 151-163.
Graham, F. L., et al.: "A New Technique for the Assay of Infectivity of Human Adenovirus 5 DNA", *Virology*, 52, (1973), pp. 456-467.
Platt, K. B., et al.: "Differentiation of Vaccine Strains and Field Isolates of Pseudorabies (Aujeszky's Disease) Virus: Trypsin Sensitivity and Mouse Virulence Markers", *Archives of Virology*, 63, (1980), pp. 107-114.
Lomniczi et al., *J. Virol.*, 61, (1987), pp. 796-801.
Feldman et al., *J. Gen. Virology*, 54, (1981), pp. 333-342.
Golais et al., *Acta Virol.*, 21, (1977), pp. 25-30.
R. Skoda, *Acta Virol.*, 6, (1962), p. 189.
V. G. Tatarov, *Zbl. Vet Med.*, 15, (1968), pp. 846-853.
Berns et al., *J. Virology*, 53, (1985), pp. 89-93.
Quint et al., *J. Gen. Virology*, 68, (1987), pp. 523-534.

Primary Examiner—Elizabeth C. Weimar
Assistant Examiner—Christopher Low

[57] ABSTRACT

A thymidine kinase deficient live deletion mutant of pseudorabies virus is provided. The mutant, designated PRV783 was derived from the live deletion mutant strain 2.4N3A by deleting a 19 bp sequence from the BamHI fragment 11 of strain 2.4N3A into which had been inserted an EcoRI restriction site at a unique cleavage site in fragment 11 for the restriction endonuclease XhoI. The 19 bp deletion encompasses the inserted EcoRI site in fragment 11 of strain 2.4N3A. PRV783 is useful for preparing vaccine compositions to immunize susceptible animals against infection by pseudorabies virus.

8 Claims, 6 Drawing Sheets

DELETION MUTANT OF PSEUDORABIES VIRUS AND VACCINE CONTAINING SAID VIRUS

This application is a continuation-in-part of U.S. patent application Ser. No. 044,043, filed May 1, 1987 now abandoned, which is a continuation of U.S. patent application Ser. No. 660,097 filed Oct. 12, 1984, now U.S. Pat. No. 4,680,176.

BACKGROUND OF THE INVENTION

The invention relates to a live deletion mutant of a pseudorabies virus (PRV), also called Aujesky's disease virus (ADV). Pseudorabies is a disease of all domestic animals with the exception of the horse, and causes severe damage, especially among swine and cattle. The pig is the natural host of the herpes virus of Aujesky's disease. In pigs, PRV infection may cause respiratory illness and encephalitis, which can ultimately lead to death.

Animals are infected with PRV via a nasal route. After initial virus multiplication in the mucous membranes of the upper respiratory and digestive tracts, the virus spreads via nerves to the brain. The severity of the infection may vary from acute to sub-clinical, being mainly dependent on the virulence of the virus and the age of the infected animal. Like other herpes virus, PRV induces latent infections, particularly in nerve tissue.

Vaccination against Aujesky's disease is carried out to limit the economic damage caused by mortality and growth retardation in infected animals. For this purpose, vaccines based on attenuated live virus and on inactivated virus are available. Attenuated live virus vaccines are generally preferred, since they are more easily produced and therefore less expensive than inactivated virus. Moreover, attenuated live virus vaccines can be administered intranasally which provides better protection than parenteral vaccination with either attenuated live virus or inactivated virus.

Early vaccines based upon attenuated live virus strains possessed several disadvantages. For example, these vaccine strains were generally produced by serially passaging virulent or mildly virulent strains in tissue culture (50-900 passages), which induced uncontrolled mutation in the virus. As a result, the compositions of such vaccines were not homogeneous and viral variants of unknown virulence and vaccinating power were included in the mixtures. Moreover, such vaccines suffered from a risk of reverting to virulence which could induce latent infections.

The development of techniques for controlled manipulation of genetic material has allowed the possibility of obtaining attenuated live virus vaccines which avoid these disadvantages. The structure of the PRV genome has been described in the literature (Virology 97, 151-163 (1979)). The PRV genome contains about 160,000 nucleotide pairs containing two inverted repeats and two unique sequences, one small and one large, designated $U_s$ and $U_1$, respectively. On the basis of the arrangement of its reiterated DNA sequence, PRV has been classified as a D-herpes virus.

Various studies also reported that a functional thymidine kinase gene was required for the development of undesirable latent infections. Thymidine kinase deficiency was therefore used as a marker in the selection of useful vaccine strains. Subsequently, Kit et al. described virus strains formed by selective mutation in the thymidine kinase gene, including the formation of deletion mutants. (U.S. Pat. Nos. 4,514,497 and 4,609,548 to Kit et al.)

U.S. Pat. No. 4,680,176 to Berns et al., which is incorporated herein by reference, describes vaccine strains of PRV showing reduced virulence which contain either or both of two deletion mutations in two selected regions of the genome. The especially preferred strain of Berns et al. is strain 2.4N3A which contains an approximately 100 bp deletion in an inverted repeat sequence and a 2.4 Kbp deletion in $U_s$. Other vaccine strains of Berns et al. may additionally include a deletion in the thymidine kinase gene, preferably of 100-500 base pairs (bp) in size.

SUMMARY OF THE INVENTION

The present invention provides an improved strain of pseudorabies virus (PRV) for use in vaccinating susceptible animals against PRV infection. The strains of the invention are thymidine kinase deficient live deletion mutants of a pseudorabies virus having a genome of about 160,000 bp, said genome comprising (a) two inverted repeats, each of which contains cleavage sites for restriction endonucleases BamHI and KpnI, BamHI digestion of the genome yielding two pairs of restriction fragments derived from the sequence of the inverted repeats, a larger fragment of each pair being designated as BamHI restriction fragment 5; and KpnI digestion of the genome yielding two fragments, designated KpnI restriction fragment E and KpnI restriction fragment H, each of said KpnI fragments containing the distal end of one of the inverted repeats;

(b) a unique sequence, $U_s$, located between the inverted repeats, said unique sequence comprising a BamHI restriction fragment of about 7 kbp in length designated BamHI restriction fragment 7, said BamHI fragment 7 containing two cleavage sites for restriction endonucleases MluI, the first MluI site being located at about the 5' end of the fragment and the second MluI site being located about 2 kbp from the 5' end of the fragment and a cleavage site for BglII at about 5 kbp from the 5' end of the fragment, said first MluI site and said BglII site defining an MluI-BglII subfragment of BamHI fragment 7, and (c) a gene for thymidine kinase, the 3' portion of which being encoded by BamHI restriction fragment 11. These mutants contain (i) a deletion of about 100 bp in a portion of an inverted repeat which is common to BamHI fragment 5 and either KpnI fragment E or KpnI fragment H;

(ii) a deletion of about 2.4 lbp within the MluI-BglII subfragment of the BamHI fragment 7, said deletion causing the loss of the second MluI site from BamHI fragment 7; and (iii) a 19 bp deletion in the thymidine kinase gene which produces a thymidine kinase negative phenotype in the virus, said deletion being located within the BamHI fragment 11 coding for the 3' part of the thymidine kinase gene and encompassing an EcoRI restriction site inserted into the BamHI fragment 11 at the unique cleavage site for restriction endonuclease XhoI. An improved PRV strain, which has been designated PRV783 was derived from the 2.4N3A strain of PRV disclosed in U.S. Pat. No. 4,608,176, which is incorporated herein by reference.

Strain 2.4N3A as disclosed in the '176 patent is a live deletion mutant of pseudorabies virus derived from a parental PRV strain and characterized by a deletion of about 100 nucleotides in a portion of an inverted repeat and a 2.4 kbp deletion within a portion of $U_s$ defined by the cleavage sites of restriction endonucleases MluI and BolII. PRV783 is further characterized by a 19 bp deletion in the thymidine kinase gene of strain 2.4N3A, said deletion, which renders PRV783 Tk−, being located at an EcoRI site inserted into a unique XhoI restriction site in the BamHI restriction fragment 11 of PRV which encodes the 3′ part of the viral Tk gene.

It is believed that strain PRV783 will be superior to strain 2.4N3A because, unlike 2.4N3A, PRV783 has a Tk− phenotype which renders the virus unable to establish an undesirable latent infection. Strain PRV783 is a safe, immunogenic, viable strain for use in vaccination against PRV infections which does not establish a latent infection.

The invention also relates to vaccines for immunizing against PRV infection in susceptible animals which vaccines contain the live virus deletion mutant strain PRV783 as immunogen together with a physiologically acceptable carrier.

BRIEF DESCRIPTION OF THE DRAWINGS

The invention will be better understood in terms of the accompanying description of the invention, examples, and appended Drawings in which.

DETAILED DESCRIPTION OF THE INVENTION

PRV783 was prepared using known techniques from the PRV mutant strain 2.4N3A described in U.S. Pat. No. 4,680,176. Strain 2.4N3A contains (1) a 2.4 Kb deletion of a DNA fragment within a MluI-BglII restriction subfragment of BamHI fragment 7 which defines the short unique sequence $U_s$ and (2) an approximately 100 bp deletion in an inverted repeat sequence.

Figure 1:
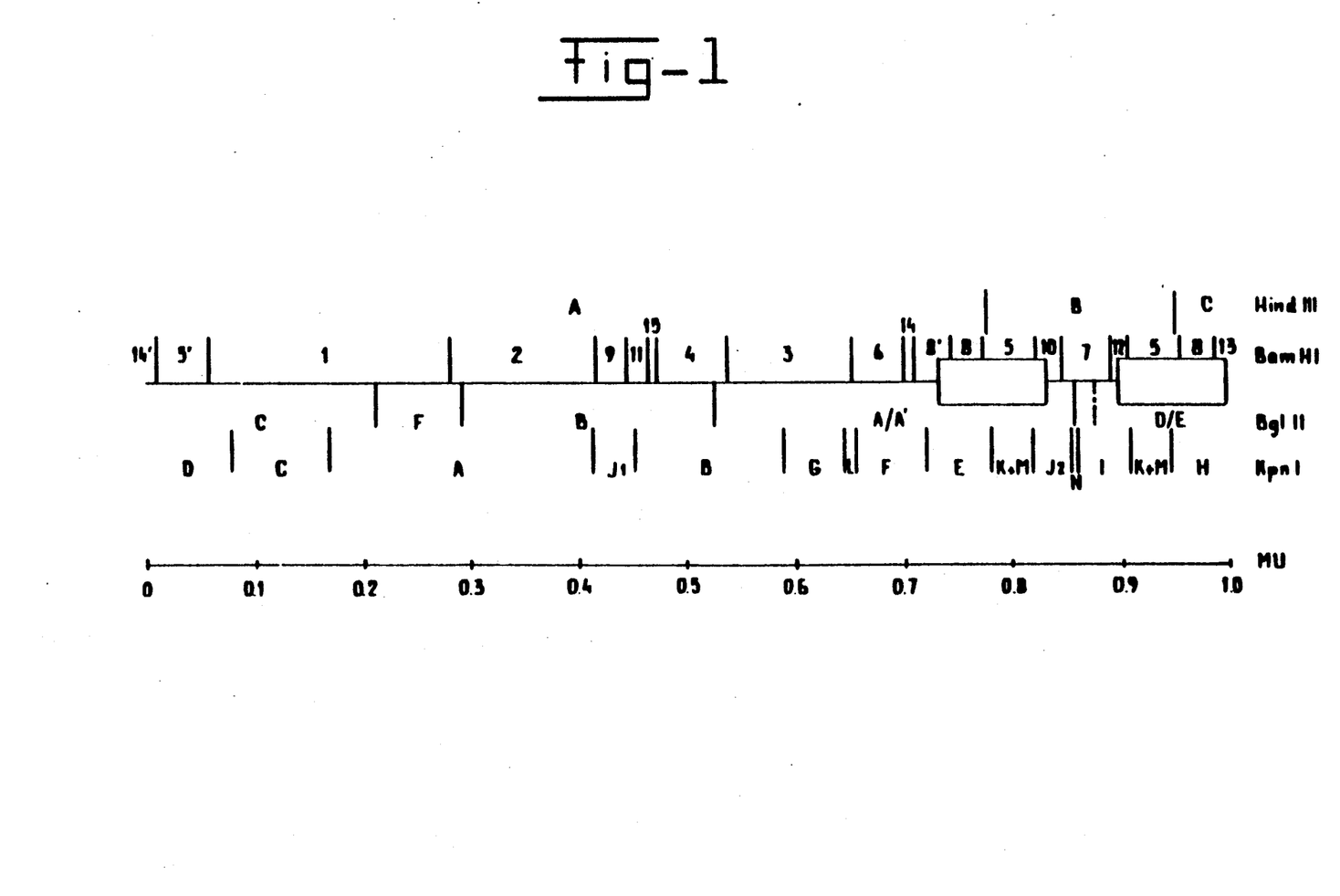
FIG. 1 is a restriction map of PRV showing the DNA cleavage fragments produced by digestion of the viral genome with the restriction endonucleases HindIII, BamHI, BglII and KpnI.
Figure 2:
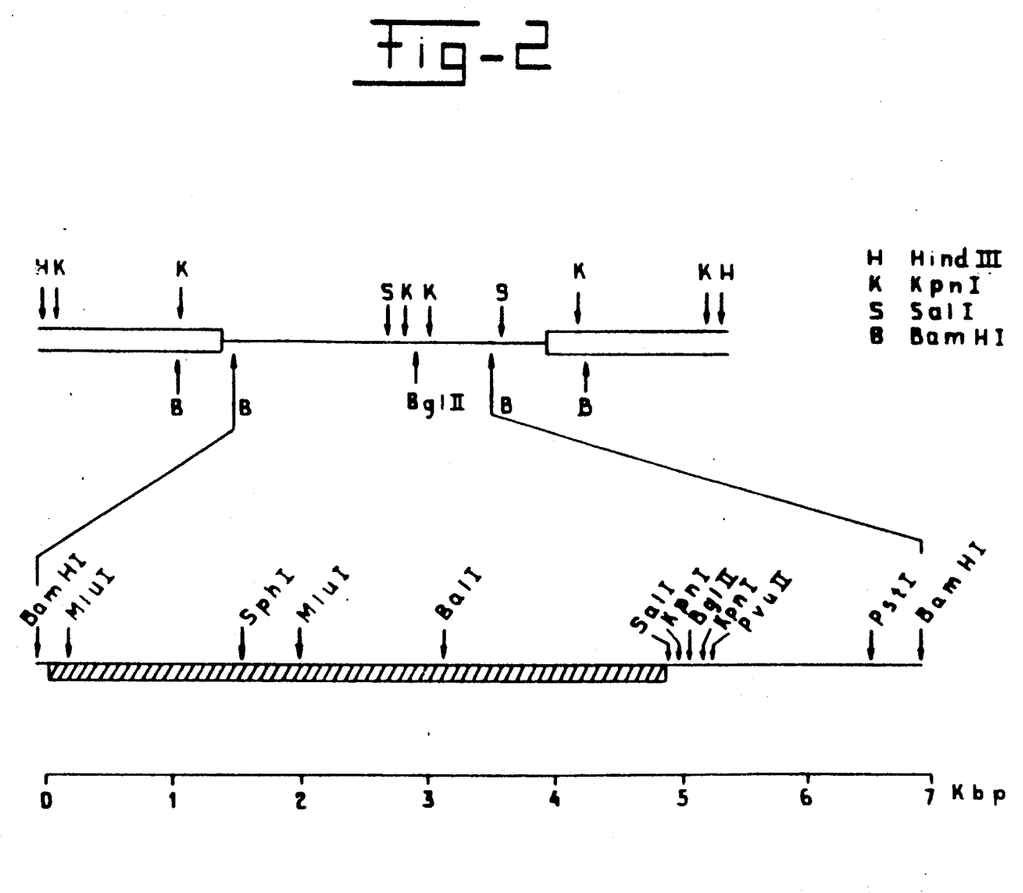
FIG. 2 is a restriction map of the BamHI fragment 7 of PRV.
Figure 3:
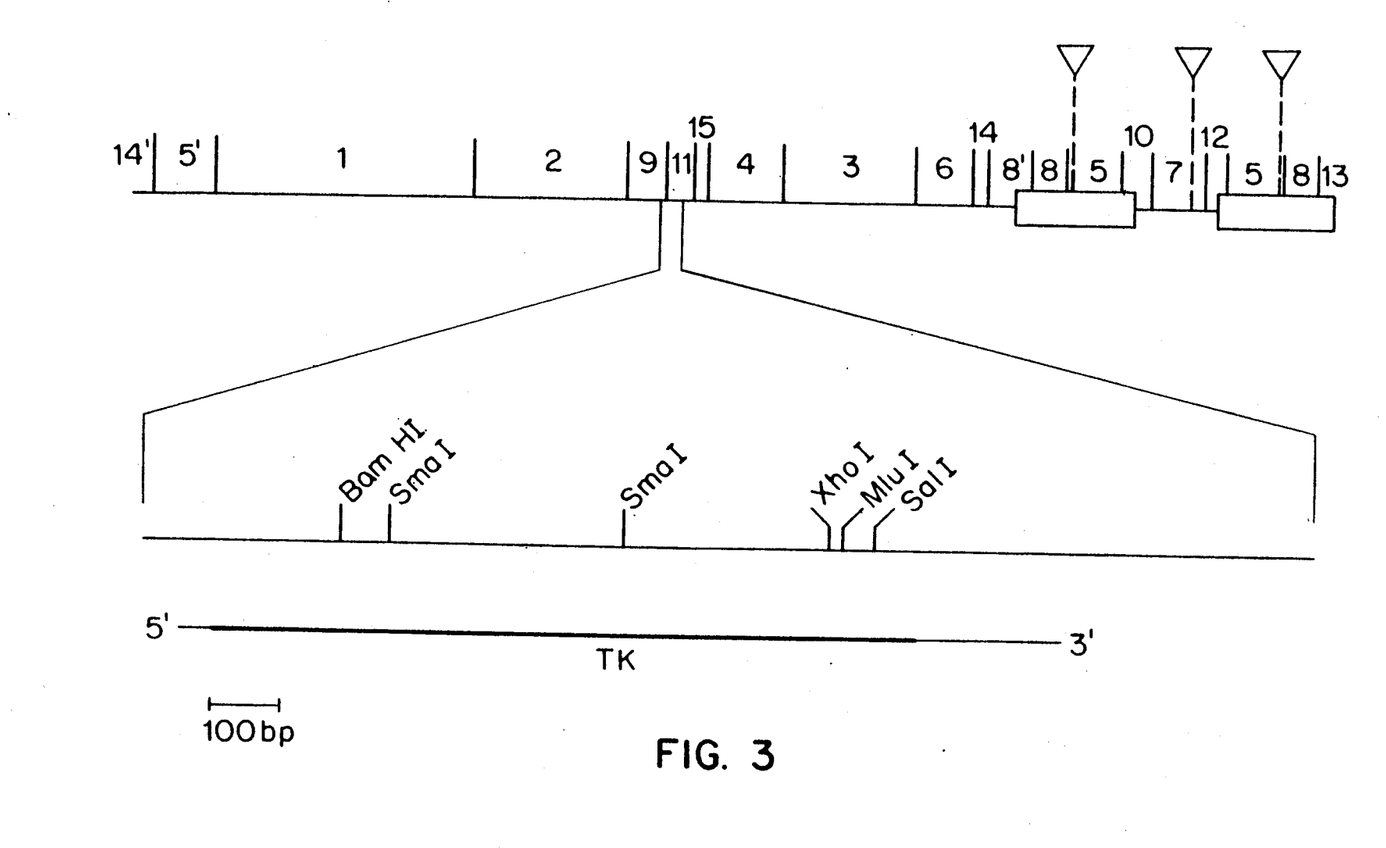
FIG. 3 is a restriction map of the genomic region of PRV strain NIA-3 comprising the thymidine kinase gene.

Strain 2.4N3A was derived from a parental strain of PRV, the genome of which consists of about 160,000 base pairs (bp) and is characterized by a restriction map as provided in FIG. 1. The cleavage sites in the genome for the restriction endonucleases BamHI, HindIII, BglII and KpnI are represented by vertical lines in FIG. 1. PRV inverted repeats are represented as rectangles. The BamHI restriction fragment 11 contains the 3′ portion of the Tk gene, while the BamHI restriction fragment 7, which is approximately 7 kbp in length, is located in the $U_s$ sequence. FIG. 2 provides a restriction map of BamHI fragment 7 showing the cleavage sites within fragment 7 generated by several restriction endonucleases, including MluI and BglII.

With reference to FIGS. 1 and 2, digestion of the parental genome yields two pairs of restriction fragments derived entirely from the sequence of the inverted repeats. The larger segment of each pair is designated as BamHI fragment 5. KpnI digestion of the genome results in two fragments designated KpnI fragments E and H, respectively, each of which contains the distal end of one of the inverted repeats. The PRV genome also contains a unique sequence $U_s$ located between the inverted repeats. $U_s$ comprises about a 7 kbp BamHI fragment which has been designated as BamHI fragment 7.

The deletions in the PRV genome in strain 2.4N3A are an approximately 100 bp portion of an inverted repeat which is common to BamHI fragment 5 and either KpnI fragment E or KpnI fragment H (FIG. 1) and a 2.4 kbp portion of $U_s$ (BamHI fragment 7) within a MluI-BglII subfragment of BamHI fragment 7 defined by the first of two cleavage sites of restriction endonuclease MluI at about the 5′ end of fragment 7 and by a cleavage site for BglII at about 5 Kbp from the 5′ end of fragment 7 (FIG. 2). The 2.4 Kbp deletion in the MluI-BglII subfragment is missing the second MluI cleavage site in fragment 7 which is located about 2 Kbp from the 5′ end of fragment 7 (FIG. 2).

The novel strain PRV783, which is derived from 2.4N3A, contains the deletions of 2.4N3A plus an additional 19 bp deletion in the BamHI fragment 11 comprising the 3′ part of the Tk gene of strain 2.4N3A. The 19 bp deletion encompasses an EcoRI restriction site which was inserted at the unique XhoI site in BamHI fragment 11 of strain 2.4N3A.

Deletion mutant PRV783 having the above-described properties is obtained by introducing deletions into the viral genome, by means of molecular biological techniques, namely in one of the following ways:

(a) Digesting cloned or uncloned subgenome fragments with restriction endonucleases and then religating part of the so generated fragments thereby deleting a fragment or fragments in the respective subgenome fragment, introducing a fragment so modified, optionally after ligation with the rest of the overlapping or not-overlapping genetic information of the viral genome, into susceptible cells, so as to produce the modified virus.

(b) Digesting cloned or uncloned subgenome fragments with restriction enconucleases and effecting a deletion at the cleavage site by treating the fragments with an exonuclease and, optionally after religation with the rest of the overlapping or not-overlapping genetic information of the viral genome, introducing the modified fragments into susceptible cells, so as to produce the modified virus.

(c) Digesting cloned or uncloned subgenome fragments with restriction endonucleases and effecting a deletion at the cleavage site by transfecting the generated fragments (without preliminary ligation), together with the rest of the overlapping or not-overlapping genetic information of the viral genome, into susceptible cells. These cells will produce the modified virus. The deletion will be effected spontaneously during the transfection procedure.

Most of the recombinant DNA methods employed in the present invention for producing PRV783 are standard procedures, well known to those skilled in art, and described in detail, for example in Maniatis et al., *Molecular Cloning,* Cold Spring Harbor Laboratory, (1982) and D. M. Glover, *DNA Cloning,* Volume I, IRL Press Limited (1985). Restriction enzymes, DNA modifying enzymes, primers, linkers, vectors, *E. coli* strains and reagents were purchased either from Boehringer Mannheim, Bethesda Research Laboratories, Pharmacia or New England Biolabs.

The following Examples illustrate the construction of strain PRV783 according to the invention, as well as its biological properties and are not meant in any way to limit the scope of the invention.

EXAMPLE 1

Subcloning of the BamHl Restriction Fragment 11 And Insertion of An EcoRI Linker Therein a. Subcloninq of the BamHI fraqment 11

The BamHI restriction fragment 11 of PRV strain NIA-3 DNA (FIG. 3) which contains the 3'-part of the viral Tk gene, (U.S. Pat. No. 4,514,497 to Kit et al.), was fractionated from the other PRV BamHI fragments on a 0.5% agarose gel. The fragment was cut from the gel and electroeluted according to the method of H. P. Zassenhaus et al., Anal. Biochem. 125, 125–130 (1982). The fragment was ligated into the BamHI site of plasmid pBR322, which had been rendered unable to self-ligate by treatment with calf intestinal alkaline phoshatase (CIP). The transformation of competent *E. coli* HB101 cells was carried out according to the procedure of D. Hanahan, J. Mol. Biol. 166, 557–580 (1983). A positive clone, pN-Bll, was selected on the basis of its restriction pattern after isolation of plasmid DNA by the method of H.C. Birnboim and J. Doly, Nucl. Acids Res. 7, 1513–1523 (1979).

b. Insertion of EcoRI Linker

The insertion of EcoRI linker 5'-CCGGAATTCCGG-3' into the single XhoI site of plasmid pN-Bll is depicted in FIG. 4. Plasmid pN-Bll was digested with XhoI and the 3'-recessed termini were filled in using the Klenow fragment of DNA Polymerase I in the presence of dATP, dGTP, dCTP and dTTP. To methylate the EcoRI site of pBR322, pN-Bll was treated with EcoRI methylase in the presence of S-adenosylmethionine. The linker was then inserted using T4 DNA ligase. After excessive digestion with EcoRI the DNA was fractionated on a low melting temperature agarose gel. The appropriate band was cut from the gel, melted, diluted, ligated with T4 DNA ligase and used to transform E. coli HB101 (Hanahan, supra). Clone pN-Bll/E was selected on the basis of its EcoRI restriction pattern. Upon digestion with EcoRI clone pN-Bll/E showed two bands of 2.7 kb and 4.8 kb, respectively, whereas pN-Bll was linearized at the single EcoRI site located in the pBR322 vector sequence. The site of two EcoRI bands of pN-Bll/E agreed well with the site of insertion of the EcoRI linker into pN-Bll.

EXAMPLE 2

Construction and Characterization of PRV Mutant Strain 783

PRV mutant strain 783 carries a deletion in the Tk gene rendering it negative in the expression of functional thymidine kinase. PRV 783 was derived from PRV mutant strain 2.4N3A (U.S. patent application Ser. No. 660,097 now U.S. Pat. No. 4,680,176, EPA 0141458) carrying an EcoRI site inserted within the 3' part of the viral Tk gene.

a. Construction of mutant strain 706

The 3.2 kb BamHI insert of clone pN-Bll/E was fractionated on a 1% agarose gel, cut from the gel and electroeluted (Zassenhaus et al., supra). The purified fragment was added to salt-gradient purified DNA of the mutant strain 2.4N3A and co-precipitated with salmon sperm DNA in the presence of calcium phosphate (F. L. Graham and A. J. van der Eb, Virol. 52, 456–467 (1973). The DNA precipitate was then used to transfect secondary porcine kidney (PK-2) cells which were grown in Eagles minimal essential medium (EMEM) plus 10% fetal calf serum (FCS). The cells were harvested 20 hr. post transfection and freeze-thawed twice. After clarification for 10 min. at 3000 g the supernatant containing the virus was titrated on PK-2 cells. Plaques were picked, EMEM plus 2% FCS was added and the virus was freeze-thawed. To test for the viral Tk phenotype, part of these freeze-thawed plaques was titrated on mouse Ltk- cells grown in EMEM plus 2% FCS and 50 microgram/ ml 5'-bromodeoxyuridine (BUdR) as described by W. M. Summers et al., Proc. Natl. Acad. Sci. USA 72, 4081–4084 (1975). Of approximately 100 plaque isolates tested, 5 showed a large plaque size under these conditions and thus were believed to contain Tk− virus. The remaining part of these 5 plaque-solutes was then titrated on PK-2 cells. Virus from individual plaques was isolated, plaque purified three times and tested for its Tk phenotype by plaque autoradiography after ($^3$H) thymidine labeling (R. B. Tenser et al., J. Clin. Microbiol. 17, 122–127 (1983). DNA from Tk− virus was isolated, digested with BamHI and EcoRI and analyzed on a Southern blot with the $^{32}$P-labeled DNA from the PRV BamHI restriction fragment 11 as described by Quint et al., J. Gen. Virol. 68, 523–534 (1987). PRV mutant strain 706, thus selected, has the Tk− phenotype and an EcoRI site which was located in the 3' part of the Tk gene (cf. FIG. 4).

b. Construction of PRV Mutant Strain 783

The DNA of PRV mutant strain 706 was digested with EcoRI and then used to transfect PK-2 cells (Graham and Van der Eb, supra). The cells were harvested 72 hr. post transfection and freeze-thawed twice. Virus present in the clarified supernatant was plaque purified three times and then used to infect PK-2 cells. The cellular DNA was isolated 48 hr. post infection, digested with restriction enzymes BamHI and EcoRI and analyzed on a Southern blot with the DNA of PRV BamHI restriction fragment 11 which was labeled with $^{32}$P (Quint et al., supra). In general, small deletions were observed in regenerated virus strains. In addition, virus having an apparent parent strain digestion profile and virus having large deletions were obtained.

Figure 5:
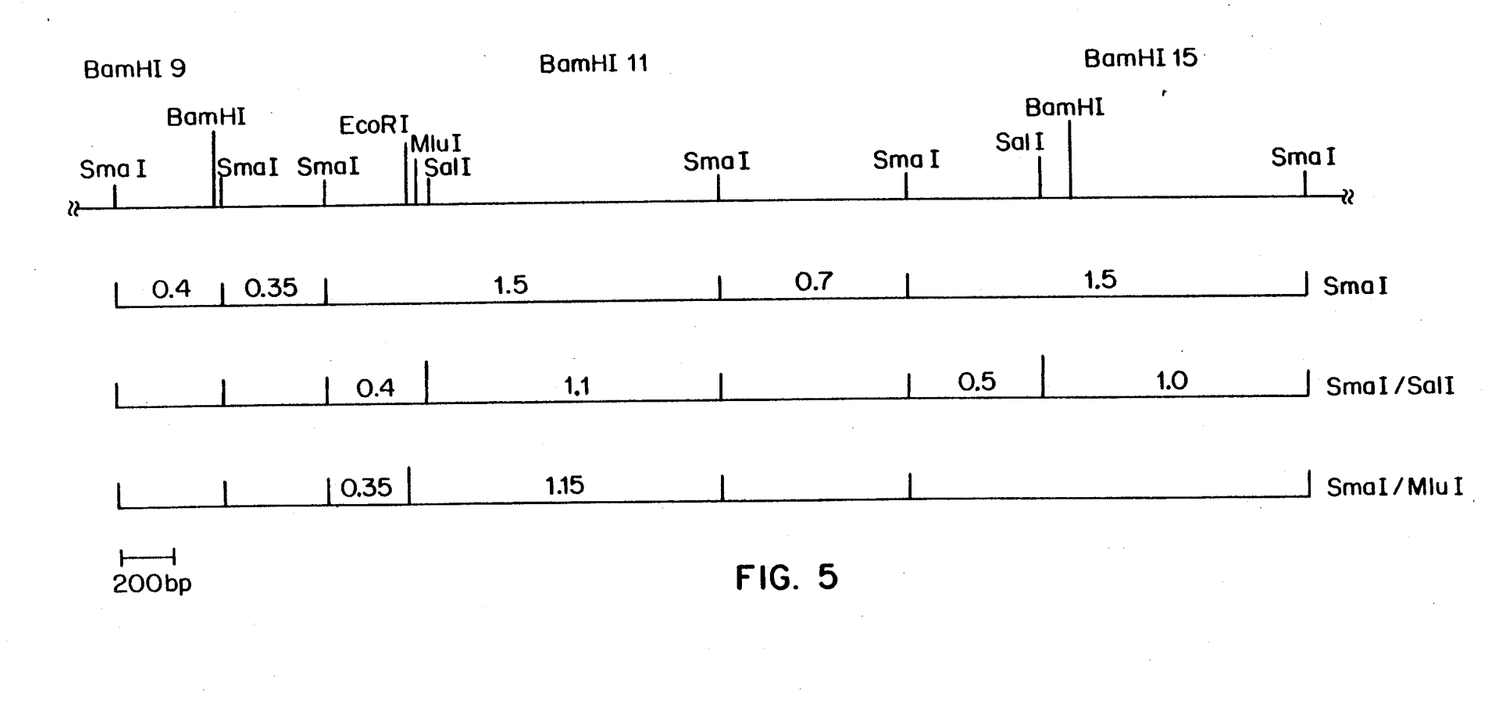
FIG. 5 is a restriction map of the BamHI restriction fragment 11 in PRV strain 2.4N3A.

PRV mutant strain 783 was selected after extension of the restriction enzyme analysis of mutants in which the EcoRI site was absent. The restriction enzyme digests performed in this analysis were: SmaI, SmaI/SalI and SmaI/MluI. The digests were analyzed on Southern blots using the 32P-labeled DNA of the PRV BamHI restriction fragment 11 (Quint et al., supra). The analysis showed that the SmaI digests of strain 2.4N3A and strain 783 hybridized to four DNA bands having a size of 1.5 kb (doublet), 0.7 kb, 0.4 kb and 0.35 kb, respectively (FIG. 5). The SmaI/SalI double digest of the two strains produced a SalI cut in the 1.5 kb SmaI doublet to give fragments of 1.1 kb, 1.0 kb, 0.5 kb and 0.4 kb (FIG. 5). In this analysis no significant difference in size was observed between the 0.4 kb SmaI/SalI fragment (which is the site of mutation) of the two strains. In the SmaI/MluI double digest of strain 2.4N3A, only one of the 1.5 kb SmaI bands was cut by MluI which produced fragments of 1.15 kb and 0.35 kb (FIG. 5). This MluI site, which is located 10 bases downstream of the XhoI site in strain 2.4N3A (Kit et al., supra) was absent in strain 783.

c. DNA Sequence Analysis of PRV Mutant Strains 706 and 783

Figure 4:
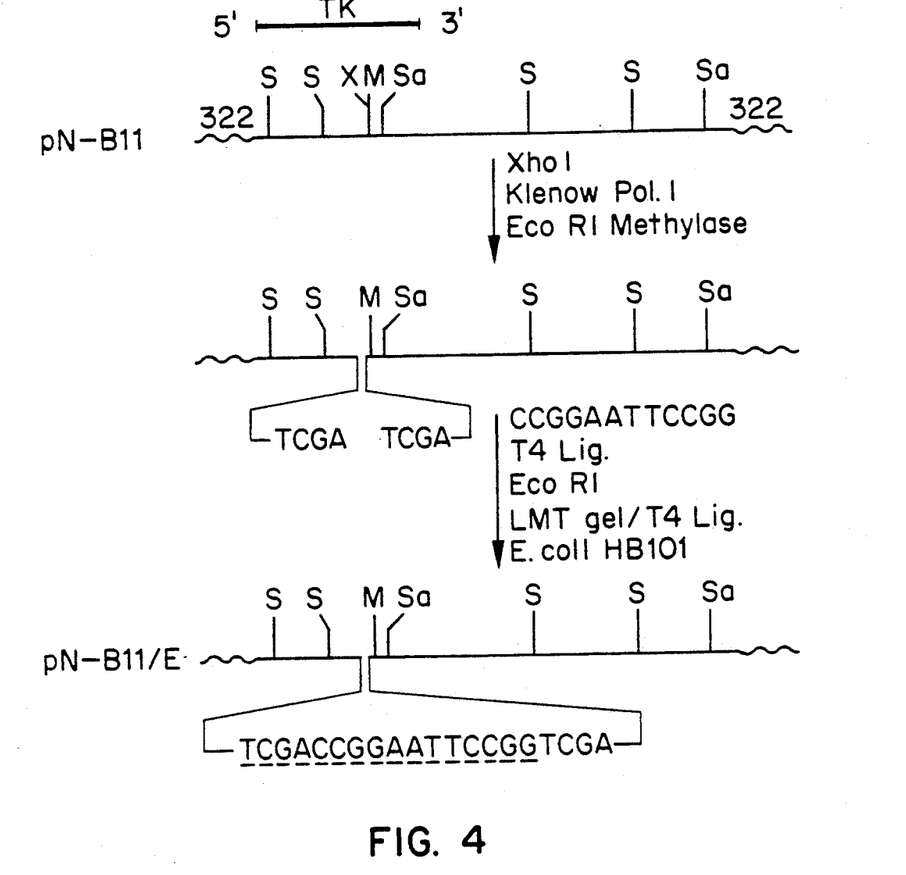
FIG. 4 shows the insertion of an EcoRI linker into the XhoI site of BamHI restriction fragment 11 cloned in plasmid pN-Bll.
Figure 6:
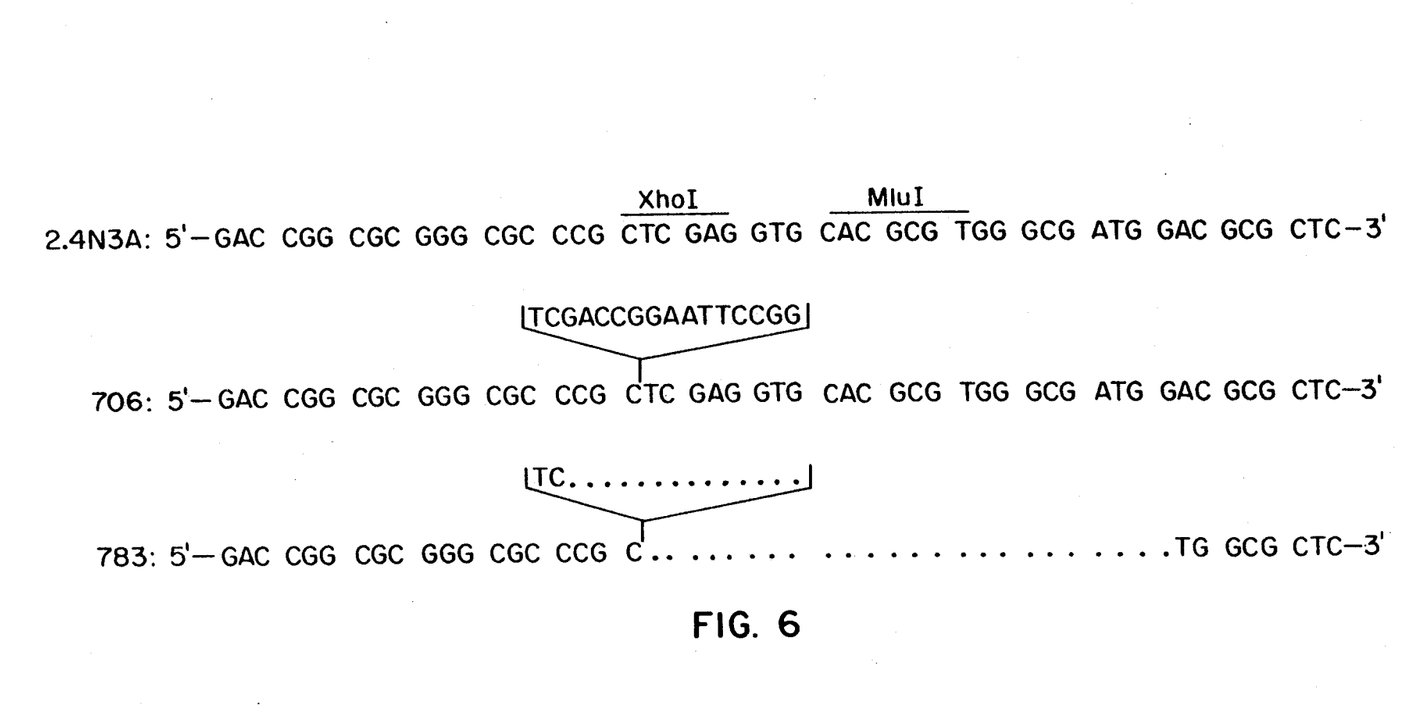
FIG. 6 is a comparison of the DNA sequence of strains 2.4N3A, PRV706 and PRV783 showing the location of the 19 bp deletion in PRV783.

The salt-gradient purified DNA of PRV strains 2.4N3A, 706 and 783 was digested with the restriction enzyme BamHI and fractionated on a 0.5% agarose gel. The 3.2 kb BamHI restriction fragment 11 was cut from the gel, electroeluted (Zassenhaus et al., supra) and ligated into the CIP-treated BamHI site of plasmid pUC19. The transformation of competent *E. coli* DH5 was carried out according to D. Hanahan (supra). Positive clones, which were selected on the basis of the restriction enzyme pattern of the insert in pUC19, were digested with SmaI and the single 1.5 kb SmaI fragment (cf. FIG. 4 and FIG. 5) was isolated by agarose gel electrophoresis and electroelution (Zassenhaus et al., supra). This fragment was digested with SalI and subcloned in the SmaI/SalI digested vector M13Mp10. Single stranded DNA of positive clones was prepared as described by J. Messing, Methods Enzymol., 101, 20–78 (1983) and sequenced according to the method of F. Sanger et al., Proc. Natl. Acad. Sci. USA 74, 54635467 (1977) using the M13 universal primer 5'-TCCCAGTCACGACGT-3'. FIG. 6 provides a comparison between the DNA sequence covering the site of the mutation in strain 706 and strain 783 and the DNA sequence of the same region of parent strain 2.4N3A. The insertion of the EcoRI linker 5'-CCGGAATTCCGG-3' according to the method described in Example 1 resulted in a net insertion of 16 bases at the XhoI site located within the 3' part of the Tk gene in strain 706. The transfection of EcoRI digested DNA of strain 706 in PK-2 cells resulted in a net deletion of 19 base pairs in strain 783 at the site of the EcoRI sequence.

EXAMPLE 3

Biological Characterization of the PRV Deletion Mutant 783 (2.4N3A Tk)

a. Safety and Latency of PRV783

In order to confirm the safety of the PRV deletion mutant 783 (2.4N3A Tk−), each of 6 pigs, 4 days of age, were inoculated both intranasally and intramuscularly with $10^{6.7}$ plaque-forming units (PFU) of the virus. The pigs were derived from the specified pathogen free (SPF) herd of the Central Veterinary Institute, which herd is tested frequently as being free of PRV. After inoculation, the pigs were housed in isolation pens and observed daily for the occurrence of clinical signs suggestive of Aujeszky's disease (AD).

Four days post-inoculation (PID.4) two of the pigs were sacrificed and subjected to post-mortem examination. Sections of the internal organs were taken for subsequent attempts at virus isolation. These were carried out as described previously by De Leeuw and Van Oirschot (1985), Veterinary Quarterly, 7, 191–197. Virus was isolated from both lung and tonsil tissues from these two pigs. During an observation period of 21 days (PID.0 to PID.21), no clinical signs suggestive of AD were observed in the other four test pigs, although it was noted that on the second day post-inoculation (PID.2) the pigs were quieter than normal. The results of body temperature readings taken post-inoculation are shown in Table A below.

TABLE A

| Pig. No. | Days post inoculation | | | | | | | | | | |
|---|---|---|---|---|---|---|---|---|---|---|---|
| | 0 | 1 | 2 | 3 | 4 | 5 | 6 | 7 | 8 | 9 | 10 |
| 121 | 38.0 | 39.2 | 39.5 | 38.6 | 38.7 | 38.9 | 39.2 | 38.1 | 38.8 | 38.7 | 38.8 |
| 123 | 38.4 | 39.0 | 38.9 | 38.6 | 38.3 | 38.8 | 38.2 | 38.5 | 38.3 | 38.3 | 37.7 |
| 124 | 38.1 | 39.0 | 39.7 | 38.9 | 38.7 | 38.6 | 38.8 | 38.5 | 38.6 | 38.5 | 38.4 |
| 126 | 38.4 | 39.4 | 39.7 | 38.8 | 38.7 | 39.2 | 38.9 | 38.6 | 38.8 | 38.4 | 38.6 |

The results of this experiment permit the conclusion that PRV 783 could be safely administered to AD-seronegative pigs younger than one week of age.

In order to establish whether or not PRV783 would remain latent in inoculated pigs, the four test pigs 121, 123, 127 and 126 were subjected to immunosuppressive therapy, using prednisolone, for four consecutive days commencing on PID.46 as described by Van Oirschot and Gielkens (1984), American Journal of Veterinary Research, 45, 567–571. In addition, two AD-seronegative SPF pigs were introduced into the isolation quarters on PID.46 to act as in-contact, sentinel controls.

Oropharyngeal swabs were taken daily from all pigs during the period PID.46 to PID.70. The swabs were cultured in an attempt to isolate virus from them. All pigs were observed daily during the same period for the occurrence of clinical signs suggestive of Aujeszky's disease. Venous blood samples were periodically taken from all pigs. Plasma samples, prepared by centrifugation of the blood, were examined for the presence of neutralizing antibodies against PR virus. In addition, blood samples had been obtained from the four original test pigs on the day of virus inoculation and at 21 days thereafter.

On PID.70 the four PRV783-inoculated pigs were sacrificed and examined post-mortem. At this time sections of brain (cerebrum, cerebellum, brain stem and medulla oblongata), tonsil, lung and mandibular lymph nodes were taken and subjected to attempts at virus isolation. Explant cultures of trigeminal ganglia were also examined as described by Van Oirschot and Gielkens (1984), American Journal of Veterinary Research, 45, 567–571.

Results

During the observation period PID.46 to PID.70 no specific clinical signs of AD infection were observed, although the inoculated pigs did show a slight rise in body temperature (maximum 40.2° C.) lasting 1–4 days. Pig number 126 also had diarrhoea on PID.49. PRV was not isolated from any of the oropharyngeal swabs examined. In addition, none of the tissue specimens obtained post-mortem from the four virus-inoculated pigs yielded any virus. There was also no increase in neutralizing antibody titres to PRV in the four inoculated pigs in the period post-immunosuppression (PID.46-PID.70). Furthermore, the in-contact sentinel pigs remained AD seronegative throughout the observation period.

The results are shown in Table B below.

TABLE B

PRV neutralizing antibody, titers after PRV 783 inoculation of 4 day old pigs, and after prednisolone treatment.

| Pig. No. | Days after inoculation | | | | |
|---|---|---|---|---|---|
| | 0 | 21 | 46[a] | 53 | 60 | 70 |
| 121 | — | 1.7[b] | 2.0 | 2.0 | 1.8 | 1.8 |
| 123 | — | 2.3 | 2.1 | 2.4 | 2.3 | 2.5 |
| 124 | — | 2.4 | 2.6 | 2.6 | 2.3 | 2.3 |
| 126 | — | 1.5 | 2.1 | 2.1 | 2.1 | 1.8 |
| 82[c] | — | — | — | — | — | — |
| 83[c] | — | — | — | — | — | — |

[a]PVD.46, start of prednisolone treatment for 4 consecutive days
[b]$\log_{10}$ virus neutralizing titer
[c]"sentinel" pigs (in-contact controls).

Conclusions

The results clearly indicate that there was no evidence for re-activation of any latent PRV783 in the immuno-suppressed pigs. It is believed that, PRV783 is incapable of inducing a latent state in young pigs.

EXAMPLE 4

Efficacy and Safety of PRV783 as a Vaccine against Aujeszky's Disease

The efficacy of PRV783 as a vaccine against Aujeszky's disease was evaluated using a standard test described by De Leeuw and Van Oirschot (1985), Veterinary Quarterly, 7, 191–197.

Materials and methods

The test vaccines used were experimental, live, vaccines prepared from the mutant PRV783 strain and from the master seed virus PRV2.4N3A. Two commercially available, live virus vaccines, INGELVAC®, (a vaccine strain based on the Bartha strain available from Boehringer Ingelheim, USA) and OMNIVAC®, (a vaccine strain based on PRV strain BUK-d13 available from Techamerica, USA) were used as positive controls.

SPF pigs which tested seronegative for AD antibodies were used in the test. Ten week old test pigs were divided into 5 groups (groups A–E). Each group, which consisted of 8 pigs, was housed separately in isolation pens. Group A and B pigs were each vaccinated intramuscularly with $10^5$ PFU of PRV2.4N3A and PRV783, respectively. Group C pigs each received intramuscularly one field dose (=2 ml) of the INGELVAC® vaccine and Group D pigs were each intramuscularly vaccinated with one field dose (=2 ml) of the OMNIVAC® vaccine. The pigs in Group E served as unvaccinated controls.

After vaccination the pigs in Group B (PRV783) were examined daily for a period of 12 weeks for clinical signs suggestive of Aujeszky's disease. Body temperatures were regularly taken and body weight was also regularly recorded. Oropharyngeal swabs were taken daily during the period between the day of vaccination (PVD.0) and 10 days post-vaccination (PVD.10). These swabs were cultured as described in Example 3 in order to isolate virus. Blood samples were taken from all vaccinated pigs during the post-vaccination observation period. These were subsequently examined for neutralizing antibodies against PRV.

At twelve weeks post-vaccination, all pigs in all groups were challenged by the intranasal instillation of $10^5$ PFU of virulent PRV (NIA-3 virus). A total observation period of 20 days was then followed during which time oropharyngeal swabs, blood samples and other clinical data were taken and recorded.

a. Period between Vaccination and Challenge

No clinical signs of Aujeszky's disease were observed in the Group B (PRV783 immunized) pigs during the observation period. Body temperatures in this group never exceeded 40° C. and weight gain was normal. PRV could not be re-isolated from any of the oropharyngeal swabs examined and a seronegative sentinel pig which was introduced into the group remained seronegative throughout the observation period. Neutralizing antibodies to PRV could be detected in this group at one week post-vaccination. Mean titers recorded were $\log_{10}$ 1.5 at 2 weeks post-vaccination and $\log_{10}$ 1.6 at twelve weeks post-vaccination (day of challenge). Mean titers ($\log_{10}$) found in the other groups at 2 weeks post-vaccination were:

Group A (PRV2.4N3A): 1.97
Group C (INGELVAC®): 0.86
Group D (OMNIVAC®): 0.86 b. Period after Challenge

During this period specific clinical signs of Aujeszky's disease were noted in the negative control pigs (Group E). Fever was observed from post-challenge day 3 (PCD.3). In addition, the pigs were anorexic and exhibited vomiting and nasal discharge. The majority of the pigs in Group E experienced respiratory distress. Nervous signs were not observed, however, and there was no mortality. From PCD.10 onwards the clinical signs had abated. The most relevant data from Group E are elaborated in Table C below.

In contrast no clinical signs suggestive of AD infection were observed in the Group B (PRV783 immunized) pigs during the observation period, although four of the pigs did show slight inappetance of a transient nature. Body temperature recorded in this group never exceeded 40° C. and only one of the eight pigs experienced a slight, transient retardation in growth, although the mean days of growth retardation for Group B pigs as a whole was zero (cf. 14 days for Control Group E). Only four of the eight pigs in Group B (PRV783) showed a fourfold or greater rise in neutralizing antibody titre post-challenge. Additionally, no evidence of excretion of the challenge virus could be found in oropharyngeal swabs taken post-challenge (PCD.0-PCD.10) from the PRV783 vaccinated pigs.

The absence of fever, growth-retardation, virus excretion and rise in serum neutralizing antibody titre, i.e. complete protection against challenge exposure, has been previously found in pigs surviving an infection with the highly immunogenic PRV strain NIA-3 (Van Oirschot et al; CEC Seminar on "Immunity to Herpes Virus Infection of Domestic Animals," Brussels, Dec. 4–5, 1984, EUR 9737 EM, 1985, pp. 281–290.

In the standard protection described in the present application complete protection against challenge exposure was also conferred by PRV 2.4N3A (Group A).

Further data relating to the post-challenge period in all the Groups are given in Table C.

TABLE C

Summarized results of standardized tests to evaluate the efficacy of PRV vaccines

| Group | Vaccine | Mean SN-titer at challenge ($log_{10}$) (a) | No. died/No. tested | Challenge results mean days of: growth arrest | fever (b) | virus shedding |
|---|---|---|---|---|---|---|
| A | 2.4N3A (c) | 2.3 | 0/8 | 0 | 0 | 0 |
| B | 783 | 1.6 | 0/8 | 0 | 0 | 0 |
| C | INGELVAC ® | 1.6 | 0/8 | 7 | 2 | 2 |
| D | OMNIVAC ® | 1.5 | 0/8 | 8.5 | 3 | 2 |
| E | Controls | — | 0/8 | 14 | 7 | 7 |

(a) SN: serum-neutralization
(b) Fever: body temperature above 40° C.
(c) The PRV 2.4N3A virus conferred complete protection against challenge exposure i.e. no clinical signs of Aujeszky's disease and no rise in SN-antibody titer after challenge.

Conclusion

The results of this standard protection test indicate that the PRV783 vaccine was highly efficacious in protecting against direct AD challenge following a single intramuscular vaccination with $10^5$ PFU of the PRV783 virus.

We claim:

1. A thymidine kinase deficient live deletion mutant of a pseudorabies virus having a genome of about 160,000 bp, said genome comprising
   (a) two inverted repeats, each of which contains cleavage sites for restriction endonucleases BamHI and KonI, BamHI digestion of the genome yielding two pairs of restriction fragments derived from the sequence of the inverted repeats, a larger fragment of each pair being designated as BamHI restriction fragment 5; and KpnI digestion of the genome yielding two fragments, designated KpnI restriction fragment E and KpnI restriction fragment H, each of said KpnI fragments containing the distal end of one of the inverted repeats;
   (b) a unique sequence, $U_s$, located between the inverted repeats, said unique sequence comprising a BamHI restriction fragment of about 7 kbp in length designated BamHI restriction fragment 7, said BamHI fragment 7 containing two cleavage sites for restriction endonucleases MluI, the first MluI site being located at about the 5' end of the fragment and the second MluI site being located about 2 kbp from the 5' end of the fragment and a cleavage site for BglII at about 5 kbp from the 5' end of the fragment, said first MluI site and said BglII site defining an MluI-BglII subfragment of BamHI fragment 7, and
   (c) a gene for thymidine kinase, the 3' portion of which being encoded by BamHI restriction fragment 11, said thymidine kinase deficient deletion mutant containing
      (i) a deletion of about 100 bp in a portion of an inverted repeat which is common to BamHI fragment 5 and either KpnI fragment E or KpnI fragment H;
      (ii) a deletion of about 2.4 kbp within the MluI-BglII subfragment of the BamHI fragment 7, said deletion causing the loss of the second MluI site from BamHI fragment 7; and
      (iii) a 19 bp deletion in the thymidine kinase gene which produces a thymidine kinase negative phenotype in the virus, said deletion being located within the BamHI fragment 11 coding for the 3' part of the thymidine kinase gene and encompassing an EcoRI restriction site inserted into the BamHI fragment 11 at the unique cleavage site for restriction endonuclease XhoI.

2. A thymidine kinase deficient live deletion mutant of pseudorabies virus according to claim 1 derived from the mutant pseudorabies virus strain 2.4N3A by deleting a 19 bp sequence from the BamHI fragment 11 of strain 2.4N3A into which had been inserted an EcoRI restriction site at a unique cleavage site for the restriction enzyme XhoI, said deletion encompassing the EcoRI restriction site.

3. A thymidine kinase deficient live deletion mutant of pseudorabies virus according to claim 2 designated PRV783.

4. A vaccine for prevention of pseudorabies virus infection in susceptible animals comprising an immunogenic amount of the thymidine kinase deficient live deletion mutant of pseudorabies virus designated strain PRV783 together with a physiologically acceptable carrier.

5. A vaccine according to claim 4 for administration to pigs.

6. A method of vaccinating susceptible animals against pseudorabies virus infection comprising administering to said animals an immunogenically effective amount of a vaccine comprising a thymidine kinase deficient live deletion mutant of pseudorabies virus designated strain PRV783 together with a physiologically acceptable carrier.

7. Method according to claim 6 for vaccinating pigs.

8. A thymidine kinase deficient live deletion mutant of a virulent pseudorabies virus having a genome of about 160,000 bp, said genome comprising
   (a) two inverted repeats, each of which contains cleavage sites for restriction endonucleases BamHI and KpnI, BamHI digestion of the genome yielding two pairs of restriction fragments derived from the sequence of the inverted repeats, a larger fragment of each pair being designated as BamHI restriction fragment 5; and KpnI digestion of the genome yielding two fragments, designated KpnI restriction fragment E and KpnI restriction fragment H, each of said KpnI fragments containing the distal end of one of the inverted repeats;
   (b) a unique sequence, $U_s$, located between the inverted repeats, said unique sequence comprising a BamHI restriction fragment of about 7 kbp in length designated BamHI restriction fragment 7, said BamHI fragment 7 containing two cleavage sites for restriction endonucleases MluI, the first MluI site being located at about the 5' end of the fragment and the second MluI site being located about 2 kbp from the 5' end of the fragment and a cleavage site for BglII at about 5 kbp from the 5' end of the fragment, said first MluI site and said BglII site defining an MluI-BglII subfragment of BamHI fragment 7, and (c) a gene for thymidine kinase, the 3' portion of which being encoded by BamHI restriction fragment 11, said thymidine kinase deficient deletion mutant containing (i) a deletion of about 100 bp in a portion of an inverted repeat which is common to BamHI fragment 5 and either KpnI fragment E or KpnI fragment H;

(ii) a deletion of about 2.4 kbp within the MluI-BglII subfragment of the BamHI fragment 7, said deletion causing the loss of the second MluI site from BamHI fragment 7; and (iii) a 19 bp deletion in the thymidine kinase gene which produces a thymidine kinase negative phenotype in the virus, said deletion being located within the BamHI fragment 11 coding for the 3' part of the thymidine kinase gene and encompassing an EcoRI restriction site inserted into the BamHI fragment 11 at the unique cleavage site for restriction endonuclease XhoI.

* * * * *

UNITED STATES PATENT AND TRADEMARK OFFICE
CERTIFICATE OF CORRECTION

PATENT NO. : 5,028,426

DATED : July 2, 1991

INVENTOR(S) : Berns et al.

It is certified that error appears in the above-identified patent and that said Letters Patent is hereby corrected as shown below:

Title page, Item 73, "Centraal Diegeneeskundig Instituut, Leystad, Netherlands" should read --Centraal Diergeneeskundig Instituut, Lelystad, Netherlands--;

Title page, 2nd col., between lines 4 and 5, insert --Tenser, Richard B., et al, "The Role of Pseudorabies Virus Thymidine Kinase Expression in Trigeminal Ganglion Infection", J. Gen. Virol., 64, (1983) pp. 1369-1373.--

Title page, 2nd col., between lines 22 and 23, insert --de Leeus, P.W., et al.: "Intranasal vaccination of pigs against Aujeszky's disease 1. Comparison of intranasal and parenteral vaccination with an attenuated vaccine in 12-week-old pigs from immunized dams", The Veterinary Quarterly, 4, No. 2 (1982), pp. 49-56.--

Col. 2, line 53, "2.4 lbp" should read --2.4 kbp--;

Col. 3, line 7, "BolII" should read --BglII--;

Col. 4, line 50, "enconucleases" should read --endonucleases--;

Col. 5, line 17, "fragment" should read --fragment--;

Col. 6, line 64, "32P-labeled" should read --32p-labeled--;

Col. 8, line 32, "127" should read --124--;

Col. 11, line 30, "KonI" should read --KpnI--.

Signed and Sealed this

Fourteenth Day of January, 1992

Attest:

HARRY F. MANBECK, JR.

Attesting Officer

Commissioner of Patents and Trademarks